United States Patent

Tanaka et al.

Patent Number: 5,804,599
Date of Patent: Sep. 8, 1998

[54] INTERLEUKIN-1 PRODUCTION INHIBITING COMPOUND

[75] Inventors: Takeo Tanaka, Machida; Eiji Tsukuda, Sunto-gun; Keiko Ochiai, Ebina; Katsuhiko Ando, Machida; Hidemasa Kondo, Kawasaki; Youichi Uosaki; Yutaka Saitoh, both of Machida; Yuzuru Matsuda, Koganei; Fumito Koizumi; Tsutomu Agatsuma, both of Machida, all of Japan

[73] Assignee: Kyowa Hakko Kogyo Co., Ltd., Tokyo, Japan

[21] Appl. No.: 534,852

[22] Filed: Sep. 27, 1995

[30] Foreign Application Priority Data

Sep. 30, 1994 [JP] Japan ................................ 6-237227
Mar. 22, 1995 [JP] Japan ................................ 7-062799

[51] Int. Cl.⁶ .......................... A01N 43/20; A01N 43/24; A01N 37/18; A61K 31/16
[52] U.S. Cl. .......................... 514/475; 514/616; 514/617; 514/619
[58] Field of Search .............. 424/278.1, 280.1, 424/282.1, 93.4, 93.43; 435/170, 132, 126, 127, 128, 253.5; 514/456, 421, 468, 469, 452, 475, 616, 617, 619, 622; 549/546, 541

[56] References Cited

U.S. PATENT DOCUMENTS

| 4,226,879 | 10/1980 | Omura et al. | 424/278 |
|---|---|---|---|
| 4,595,770 | 6/1986 | Brodasky et al. | 549/541 |
| 5,079,263 | 1/1992 | Zeeck et al. | 514/616 |
| 5,106,868 | 4/1992 | Nkano et al. | 514/475 |
| 5,114,967 | 5/1992 | Franco et al. | 514/475 |
| 5,444,087 | 8/1995 | Patel et al. | 514/475 |

FOREIGN PATENT DOCUMENTS

| 4-59743 | 2/1992 | Japan . |
|---|---|---|
| 4-74121 | 3/1992 | Japan . |
| 4-202127 | 7/1992 | Japan . |

OTHER PUBLICATIONS

Miura et al. "Induction of Apoptosis in Fibroblast by IL1 Beta Converting Enzyme, a Mammalian Homolog of the C.elegans Cell Death Gene ced–3". Cell. vol. 75, pp. 653–660, Nov. 19, 1993.

Thiericke et al. "Studies of Precursor–directed Biosynthesis with Streptomyes sp. Part 1. Isolation of Manumycin Analogues by Feeding of Aminobenzoic Acids as C7N Starter Units". J. Chem. Soc. Perkin Trans. vol. 1, pp. 2123–2127, 1988.

Hara et al. "Identification od Ras farnesyltransferase inhibitors by microbial screening". PNAS. vol. 90, pp. 2281–2285, Mar. 1993.

Shu et al. "Manumycins E, F, G, New Members of Manymycin Class Antibiotics from Streptomyces sp.". Journal of Antibiotics. pp. 324–333, Mar. 1994.

J. Org. Chem., vol. 58, No. 24, 1993, pp. 6582 to 6587.

Tetrahedron Letters, No. 50, pp. 4995 to 4998 "Manumycin" (1973).

The Journal of Antibiotics, vol. 47, No. 3 pp. 324 to 333, (1994).

The Journal of Antibiotics, vol. 36, No. 8, pp. 950 to 957 (1983).

The Journal of Antoibiotics, vol. 46, No. 6, pp. 1027 to 1030 (1990).

*Primary Examiner*—Marian C. Knode
*Assistant Examiner*—Datquan Lee
*Attorney, Agent, or Firm*—Antonelli, Terry, Stout & Kraus, LLP

[57] ABSTRACT

Provided is an Interleukin-1 production inhibiting compound represented by formula (I)

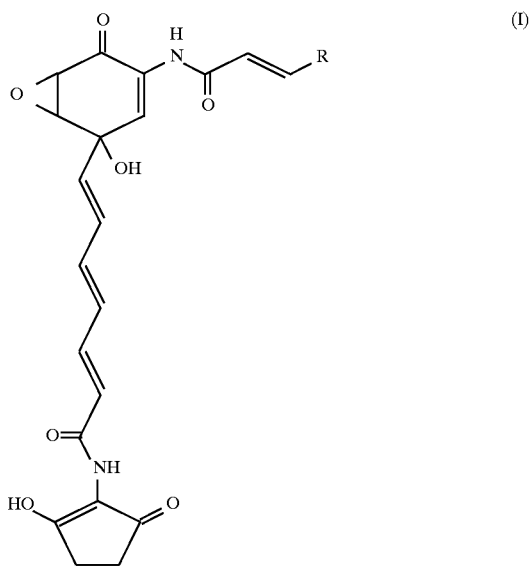

wherein R denotes 4-methyl-1-pentenyl, 5-methyl-1,3-heptadienyl or 1-methylpentanyl.

8 Claims, No Drawings

INTERLEUKIN-1 PRODUCTION INHIBITING COMPOUND

BACKGROUND OF THE INVENTION

The present invention relates to a novel Interleukin-1 production inhibiting compound which is produced from a microorganism belonging to the genus Streptomyces, and which is useful as an agent for treating diseases such as chronic rheumatism, gout, osteoarthritis, osteoporosis, periarteritis nodosa, ulcerative colitis, chronic nephritis, active chronic hepatitis, septicemia, endotoxin shock, atherosclerosis, pyrexia of infectious disease and the like and as an antibacterial agent.

Interleukin-1 (hereinafter referred to as "IL-1") is a protein which is produced from a variety of in vivo cells such as macrophage, monocyte, neutrophil, fibroblast, skin keratinocyte, hepatic Kupffer cell, renal glomerular mesangial cell, brain astroglia, angioendothelial cell and the like and which has a molecular weight of 17.5 kDa. IL-1 includes α-form having an isoelectric point (pI) of 5 and β-form having pI of 7. At present, it has been clarified that the α-form and β-form exhibit the same activity.

IL-1 is known to have various biological activities. That is, IL-1 is deemed to act as a factor that enhances multiplicative division of lymphocytes and as a cofactor that enhances multiplication of B cells and production of antibodies. Further, it is considered that IL-1 acts on arachidonic acid cascade in a temperature center of the hypothalamus to increase the synthesis of prostagrandin $E_2$, thereby causing pyrexia. Still further, it is shown that the activity of IL-1 is significantly increased in the serum of patients suffering from septicemia or Crohn's disease and on a cavum articulare of patients who suffer from rheumatism. Thus, it is suggested that IL-1 be related with attack and progress of these diseases. Suppression of the production of IL-I is considered to be effective for alleviating the diseases that occur through IL-1.

As the compound that exhibits activity of inhibiting the production of IL-1, synthetic compounds such as naphthalene derivatives [Japanese Published Unexamined Patent Application No. 59,743/1992], 3-arylisothiazole derivatives [Japanese Published Unexamined Patent Application No. 74,121/1992] and zingerol derivatives [Japanese Published Unexamined Patent Application No. 202,127/1992] are known.

The following compounds are known to exhibit antibacterial activity.

Manumycin A having the following formula is known to exhibit antibacterial activity [Tetrahedron Lett. 50, 4995 (1973)].

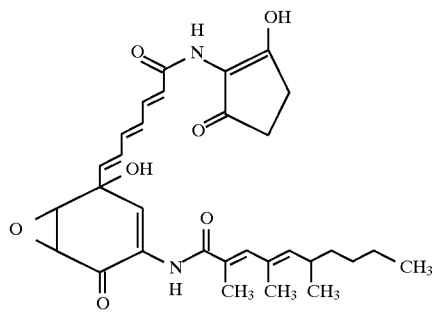

Manumycin A

Manumycins B, C and D having the following formulae are known to exhibit antibacterial activity [J. Org. Chem. 58, 6583 (1993)].

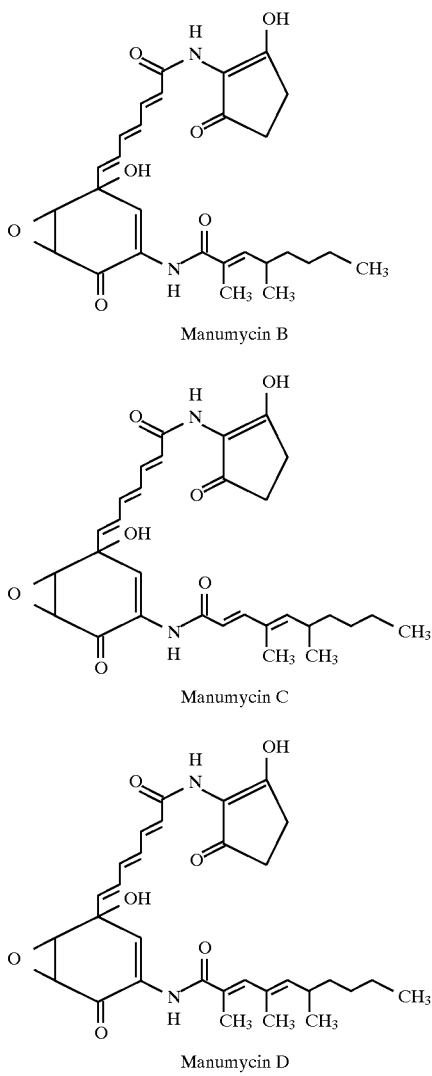

Manumycin B

Manumycin C

Manumycin D

Manumycins E and G having the following formulae are known to exhibit antibacterial activity [J. Antibiot. 47, 324, (1994)].

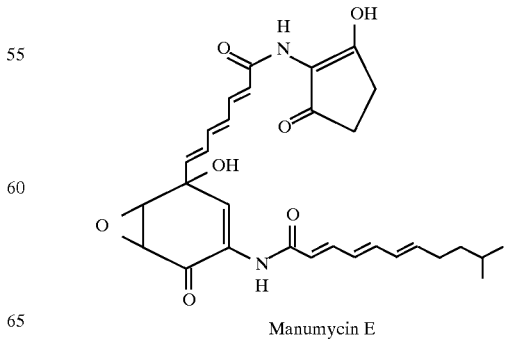

Manumycin E

-continued

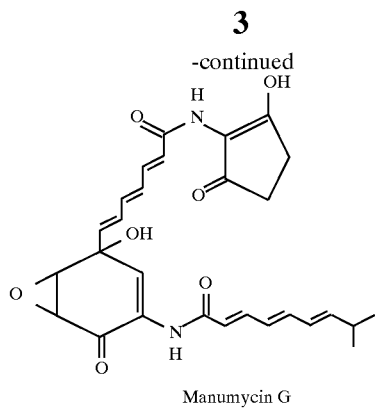

Manumycin G

U-56407 represented by the following formula is known to exhibit antibacterial activity [J. Antibiotics, 36, 950–956 (1983)]:

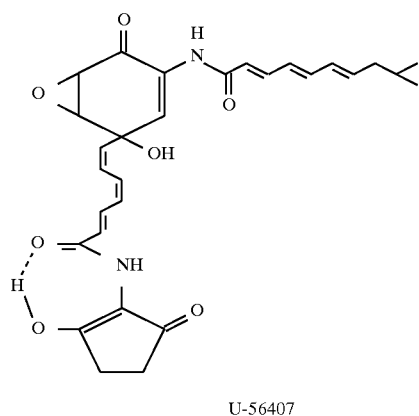

U-56407

Alisamycin represented by the following formula is known to exhibit antibacterial activity [J. Antibiotics, 46, 1027–1030 (1990)].

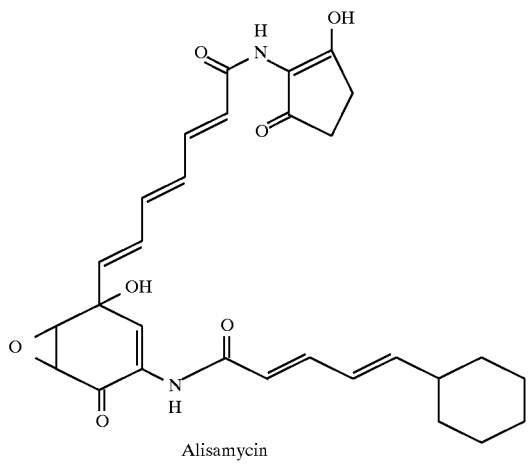

Alisamycin

SUMMARY OF THE INVENTION

It is an object of the present invention to provide novel physiologically active substances that exhibit excellent inhibiting activity of the production of IL-1 as well as excellent antibacterial activity.

The present invention provides a compound [hereinafter referred to as "Compound (I)"] represented by formula(I)

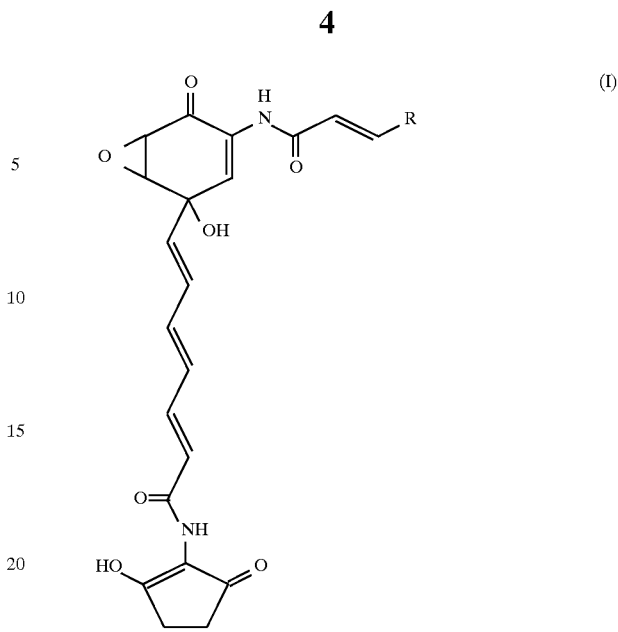

wherein R represents 4-methyl-1-pentenyl, 5-methyl-1,3-heptadienyl or 1-methylpentanyl.

Compound (I) can be obtained by culturing a microorganism belonging to the genus Streptomyces.

DETAILED DESCRIPTION OF THE INVENTION

Among Compound (I), the compound in which R is 4-methyl-1-pentenyl is named EI-1511-3, the compound in which R is 5-methyl-1,3-heptadienyl EI-1511-5, and the compound in which R is 1-methylpentyl EI-1625-2, respectively. The structural formulae and physicochemical properties of these compounds are described below.

(i) EI-1511-3

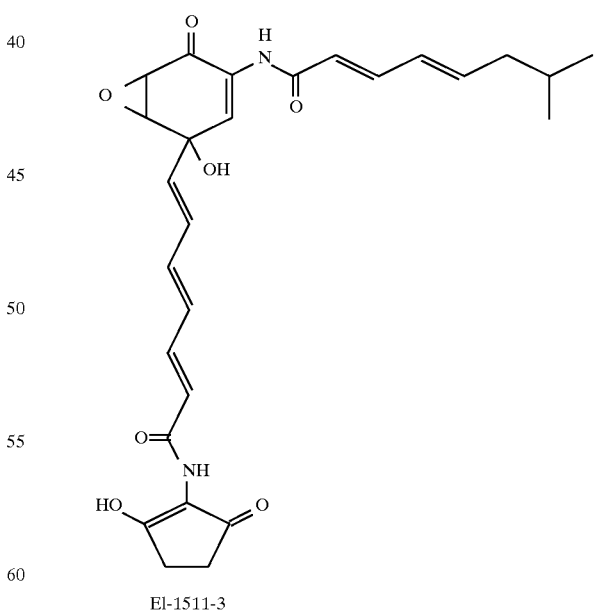

EI-1511-3

State: Yellow powder
Melting point: 165°–168° C.
Specific rotation: $[\alpha]_D^{27} = +231°$ (c=0.225, CH$_3$OH)
FABMS spectrum: m/z amu 495 (M+H)$^+$ High-resolution FABMS spectrum: m/z amu 495.2124 (M+H)$^+$, $\Delta$-0.7 mmu $C_{27}H_{31}N_2O_7$ UV spectrum (CH$_3$OH): $\lambda_{max}$ nm ($\epsilon$) 314 (42,600), 278 (58,600).

CD spectrum (CH$_3$OH): $\lambda_{max}$ nm ($\Delta\epsilon$) 314 (+14.17), 280 (−19.93).

IR spectrum (KBr): $\upsilon_{max}$ cm$^{-1}$ 3379, 1684, 1672, 1616, 1523, 1367, 1001.

$^1$H-NMR spectrum (CDCl$_3$): $\delta$ ppm (integration, multiplicity, binding constant)
13.50 (1H, br. s), 7.56 (1H, br. s), 7.55 (1H, br. s), 7.41 (1H, d, J=2.7 Hz), 7.33 (1H, dd, J=14.8, 11.2 Hz), 7.24 (1H, dd, J=14.8, 10.1 Hz), 6.59 (2H, m), 6.42 (1H, m), 6.15 (2H, m), 6.05 (1H, d, J=14.8 Hz), 5.87 (1H, m), 5.84 (1H, d, J=14.8 Hz), 3.71 (1H, dd, J=3.8, 2.7 Hz), 3.65 (1H, d, J=3.8 Hz), 3.00 (1H, br. s), 2.61 (2H, m), 2.53 (2H, m), 2.07 (2H, dd, J=6.4, 6.4 Hz), 1.72 (1H, m), 0.91 (6H, d, J=6.7 Hz).

$^{13}$C-NMR spectrum (CDCl$_3$): $\delta$ ppm (multiplicity)
197.26 (s), 188.62 (s), 173.82 (s), 165.43 (s), 165.17 (s), 144.28 (d), 143.75 (d), 143.56 (d), 139.62 (d), 136.24 (d), 131.76 (d), 131.65 (d), 129.11 (d), 128.16 (s), 126.29 (d), 121.55 (d), 120.94 (d), 114.93 (s), 71.25 (s), 57.46 (d), 53.02 (d), 42.41 (t), 32.14 (t), 28.33 (d), 25.64 (t), 22.37 (q), 22.37 (q).

Solubility: easily soluble in dimethyl sulfoxide and acetone, soluble in methanol Color reaction: positive for iodine and sulfuric acid (ii) EI-1511-5

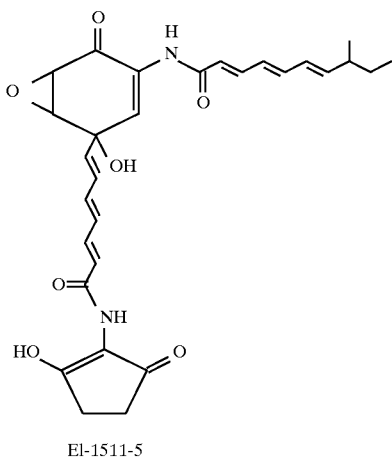

EI-1511-5

State: Yellow powder

Melting point: 194°–197° C.

Specific rotation: $[\alpha]_D^{26}$=+325° (c=0.147, CH$_3$OH)

FABMS spectrum: m/z amu 521 (M+H)$^+$

High-resolution FABMS spectrum: m/z amu 521.2289 (M+H)$^+$, $\Delta$+0.2 mmu $C_{29}H_{33}N_2O_7$ UV spectrum (CH$_3$OH): $\lambda_{max}$ nm ($\epsilon$) 309 (50,300).

CD spectrum (CH$_3$OH): $\lambda_{max}$ nm ($\Delta\epsilon$) 342 (+38.74), 300 (−52.86).

IR spectrum (KBr): $\upsilon_{max}$ cm$^{-1}$ 3313, 1687, 1653, 1620, 1608, 1539, 1527, 1371, 1001.

$^1$H-NMR spectrum (CDCl$_3$): $\delta$ ppm (integration, multiplicity, binding constant)
13.51 (1H, br. s), 7.56 (2H, br. s), 7.41 (1H, d, J=2.7 Hz), 7.33 (1H, dd, J=14.7, 11.3 Hz), 7.29 (1H, dd, J=15.0, 11.3 Hz), 6.59 (2H, m), 6.56 (1H, dd, J=15.0, 10.5 Hz), 6.42 (1H, m), 6.23 (1H, dd, J=15.0, 11.3 Hz), 6.11 (1H, dd, J=15.2, 10.5 Hz), 6.05 (1H, d, J=14.7 Hz), 5.89 (1H, d, J=15.0 Hz), 5.86 (1H, m), 5.84 (1H, dd, J=15.2, 7.9 Hz), 3.71 (1H, dd, J=3.8, 2.7 Hz), 3.65 (1H, d, J=3.8 Hz), 3.01 (1H, br.s), 2.61 (2H, m), 2.53 (2H, m), 2.14 (1H, m), 1.36 (2H, dq, J=7.3, 7.3 Hz), 1.02 (3H, d, J=6.7 Hz), 0.87 (3H, t, J=7.3 Hz).

$^{13}$C-NMR spectrum (CDCl$_3$): $\delta$ ppm (multiplicity)
197.29 (s), 188.63 (s), 173.84 (s), 165.43 (s), 165.07 (s), 146.67 (d), 143.67 (d), 143.56 (d), 142.08 (d), 139.62 (d), 136.27 (d), 131.77 (d), 131.66 (d), 128.22 (d), 128.18 (s), 127.49 (d), 126.31 (d), 121.56 (d), 121.56 (d), 114.96 (s), 71.26 (s), 57.47 (d), 53.02 (d), 38.83 (d), 32.18 (t), 29.54 (t), 25.67 (t), 19.73 (q), 11.74 (q).

Solubility: easily soluble in dimethyl sulfoxide and acetone, soluble in methanol Color reaction: positive for iodine and sulfuric acid (iii) EI-1625-2

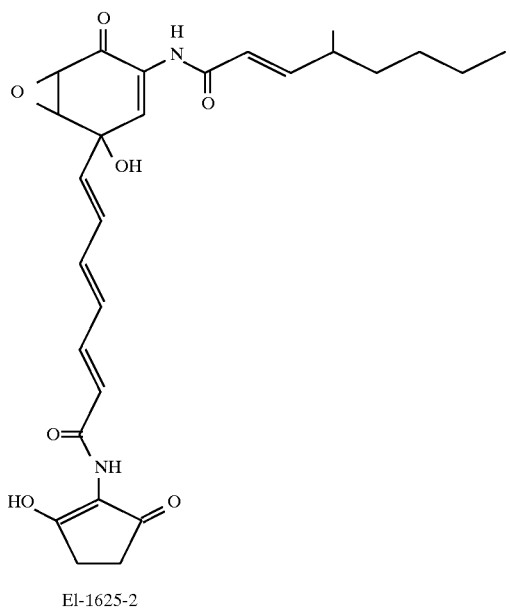

EI-1625-2

State: Yellow powder

Melting point: 105°–107° C.

Specific rotation: $[\alpha]_D^{29}$=−17.0° (c=0.1, CHCl$_3$)

Molecular formula: $C_{27}H_{32}N_2O_7$

FABMS spectrum: m/z amu 497 (M+H)$^+$

High-resolution FABMS spectrum: calculated $C_{27}H_{33}N_2O_7$: 497.2288, found 497.2277

UV spectrum (CH$_3$OH): $\lambda_{max}$ nm ($\epsilon$) 321 (37,600), 281 (32,400), 265 (31,000).

CD spectrum (CH$_3$OH): $\lambda_{ext}$ nm ($\Delta\epsilon$) 322 (−3.7), 277 (+9.9).

IR spectrum (KBr): $\upsilon_{max}$ cm$^{-1}$ 3317, 2925, 1674, 1624, 1522, 1367, 1005.

$^1$H-NMR spectrum (CDCl$_3$): $\delta$ ppm (integration, multiplicity, binding constant)
13.57(1H, br. s), 7.70(1H, s), 7.56 (1H, s), 7.40 (1H, d, J=2.5 Hz), 7.32(1H, dd, J=11.0, 14.6 Hz), 6.82 (1H, dd, J=8.1, 15.4 Hz), 6.59(2H, m), 6.41 (1H, m), 6.08 (1H, d, J=14.6 Hz), 5.85(1H, m), 5.81(1H, d, J=15.4 Hz), 3.70(1H, dd, J=2.5, 3.7 Hz), 3.64(1H, d, J=3.7 Hz), 3.32(1H, br.s), 2.59(2H, br. s), 2.54(2H, br. s), 2.30(1H, m), 1.40–1.31(2H, m), 1.30–1.19(4H, m), 1.05(3H, d, J=6.8 Hz), 0.88(3H, t, J=6.8 Hz).

$^{13}$C-NMR spectrum (CDCl$_3$): δ ppm (multiplicity)
197.4(s), 188.7(s), 174.1(s), 165.5(s), 165.0(s), 153.4(d), 143.5(d), 139.6(d), 136.3(d), 131.8(d), 131.6(d), 128.0(s), 126.7(d), 121.6(d), 121.5(d), 115.0(s), 71.2(s), 57.4(d), 53.0(d), 36.6(d), 35.8(t), 32.2(t), 29.4(t), 25.7(t), 22.7(t), 19.5(q), 14.0(q).

Rf values of Compounds (I) obtained by thin-layer chromatography under the following conditions are shown below.

Rf values:
EI-1511-3: 0.57
EI-1511-5: 0.60
EI-1625-2: 0.57
Eluent: chloroform-methanol-acetic acid (90:10:1) Thin layer: HPLC Fertigplatten Kieselgel 60 F254 (Merck Co.)
Elution method: room temperature, rising mode, 20 to 40 minutes
Detection: irradiation with UV light of 253.6 nm As apparent from the above-mentioned data, Compound (I) of the present invention is novel.

The above-mentioned data were obtained using the following instruments.

Melting point: Yanagimoto instrument for measuring the melting point of a trace amount of a sample
Specific rotation: JASCO DIP-370-model digital polarimeter
IR spectrum: JEOL JIR-RFX3001-model IR-absorption spectrophotometer
UV spectrum: SHIMADZU UV-2200-model UV-absorption spectrophotometer
CD spectrum: JASCO J-500A-model circular dichroism spectrophotometer
Mass spectrum: JEOL HX110A-model mass spectrometer
NMR spectrum: JEOL α400-model nuclear magnetic resonance meter A process for producing Compound (I) is described below.

Compound (I) is produced by cultivating in a culture medium a microorganism belonging to the genus Streptomyces which has the ability to produce Compound (I), accumulating Compound (I) in the culture, and recovering Compound (I) from the culture.

As the microorganism having the ability to produce Compound (I), any strain of the genus Streptomyces can be used so long as the strain has the ability to produce Compound (I). Further, mutants obtained by mutagenizing these strains either spontaneously or artificially, for example, through irradiation with an ultraviolet light, irradiation with X-rays or treatment with a mutation inducer are also available so long as the mutants have the ability to produce Compound (I).

Specific examples thereof include Streptomyces sp. E-1511 strain and Streptomyces sp. E-1625 strain.

The bacteriological properties of Streptomyces sp. E-1511 strain are described below.

1. Morphological properties
   1) Hyphae
      Formation of aerial hyphae: Observed
      Fragmentation and motility of aerial hyphae: Not observed
      Fragmentation and motility of substrate hyphae: Not observed
   2) Spores
      Sporulation and positions to which spores adhere: Sporulated as aerial spores
      Formation of sporangia and positions to which sporangia adhere: Not observed
      Number of spores linked on a sporophore: 10 or more
      Morphology of many spores linked: Curved or spiral
      Characteristics of spores
      Surface structure: Smooth
      Shape and size: Rod, approximately 0.6 to 0.8 μm ×0.7 to 0.9 μm
      Motility and presence of flagella: Not observed
   3) Others:
      Chlamydospores: Not observed
      Synnema: Not observed
      Pseudosporangia: Not observed
      Branching mode of hyphae: Simple branching 2. Cultural characteristics E-1511 strain grows normally or abundantly on usual synthetic or natural media, and its substrate hyphae are brown or brownish gray. On some media, the strain produces brown soluble pigments.

The characteristics in the growth conditions and colors of the strain, when the strain was cultivated on various media at 28° C. for 14 days, are shown below. The colors were designated according to the classification of colors indicated in Color Harmony Manual published by Container Corporation of America, 4th edition (1958).

1) Sucrose-nitrate agar
   Growth: Moderate
   Color of substrate hyphae: Olive gray (1½ ig)
   Formation of aerial hyphae and Color thereof: Abundant, Beige gray (3 ih)
   Soluble pigments: None
2) Glucose-asparagine agar
   Growth: Abundant
   Color of substrate hyphae: Mustard tan (2 lg) to mustard brown (2 ni)
   Formation of aerial hyphae and Color thereof: Abundant, silver gray (3 fe)
   Soluble pigments: Produced (brown)
3) Glycerol-asparagine agar
   Growth: Abundant
   Color of substrate hyphae: Clove brown (3 ni)
   Formation of aerial hyphae and Color thereof: Abundant, silver gray (3 fe)
   Soluble pigments: Produced (brown)
4) Starch-inorganic salt agar
   Growth: Abundant
   Color of substrate hyphae: Mustard brown (2 pl)
   Formation of aerial hyphae and Color thereof: Abundant, Silver gray (3 fe)
   Soluble pigments: Produced (brown)
5) Tyrosine agar
   Growth: Abundant
   Color of substrate hyphae: Mustardbrown (2 pi) to Clove brown (3 ni)
   Formation of aerial hyphae and Color thereof: Abundant, Covert gray (2 fe)
   Soluble pigments: Slightly produced (brown)
6) Nutrient agar
   Growth: Moderate
   Color of substrate hyphae: Mustard brown (2 pi)
   Formation of aerial hyphae and Color thereof: Poor, Covert gray (2 fe)
   Soluble pigments: None
7) Yeast extract-malt extract agar
   Growth: Abundant
   Color of substrate hyphae: Clove brown (3 pl)

Formation of aerial hyphae and Color thereof: Abundant, Silver gray (3 fe)
Soluble pigments: Produced (brown)

8) Oatmeal agar
Growth: Moderate
Color of substrate hyphae: Golden brown (3 pi) to Clove brown (3 pl)
Formation of aerial hyphae and Color thereof: Moderate, Ashes (5 fe)
Soluble pigments: Produced (brown)

3. Physiological properties:

The temperature range for growth indicates the results of the strain after 10-day cultivation. The remaining items indicate the results after a 2 to 3 week-cultivation at 28° C.

1) Temperature range for growth: 6.0° to 38.0° C.
2) Liquefaction of gelatin: Observed
3) Hydrolysis of starch: Observed
4) Coagulation of skim milk powder and peptonization thereof: Peptonized
5) Formation of melanoid pigment:
    (i) Peptone-yeast extract-ion agar medium: Not observed
    (ii) Tyrosine agar: Slightly formed
6) Utilization of carbon source (basic medium: Pridham Gottlieb-agar medium):

+ indicates that the strain utilizes the carbon source; − indicates that the strain did not utilize the carbon source; and W indicates that it is unclear as to whether or not the strain utilized the carbon source.

| L-Arabinose: | − |
| D-Xylose: | + |
| D-Glucose: | + |
| Sucrose: | W |
| Raffinose: | + |
| D-Fructose: | W |
| L-Rhamnose: | + |
| Inositol: | W |
| D-Mannitol: | W |

4. Chemotaxonomic properties:
    Optical isomer of diaminopimelic acid in the strain: LL-form Accordingly, the strain is classified into the genus Streptomyces of actinomycetes.

The strain was named Streptomyces sp. E-1511, and it was deposited at the National Institute of Bioscience and Human Technology of the Agency of Industrial Science and Technology under FERM BP-4792 as of Sep. 1, 1994 in terms of the Budapest Treaty.

The bacteriological properties of Streptomyces sp. E-1625 are described below.

1. Morphological properties
1) Hyphae
    Formation of aerial hyphae: Observed
    Fragmentation and motility of aerial hyphae: Not observed
    Fragmentation and motility of substrate hyphae: Not observed
2) Spores
    Sporulation and positions to which spores adhere: Sporulated as aerial spores
    Formation of sporangia and positions to which sporangia adhere: Not observed
    Number of spores linked on a sporophore: 10 or more
    Morphology of many spores linked: Curved or spiral Characteristics of spores
Surface structure: Smooth
Shape and size: Rod, approximately 0.6 to 0.7 $\mu$m ×0.7 to 0.9 $\mu$m
Motility and presence of flagella: Not observed 3) Others:
    Chlamydospores: Not observed
    Synnema: Not observed
    Pseudosporangia: Not observed
    Branching mode of hyphae: Simple branching 2. Cultural characteristics E-1625 strain grows normally or abundantly on usual synthetic or natural media, and its substrate hyphae are brown to red. On some media, the strain produces brown soluble pigments.

The characteristics in the growth conditions and colors of the strain, when the strain was cultured on various media at 28° C. for 14 days, are shown below. The colors were designated according to the classification of colors indicated in Color Harmony Manual published by Container Corporation of America, 4th edition (1958).

1) Sucrose-nitrate agar
    Growth: Moderate
    Color of substrate hyphae: Sand (2 ec)
    Formation of aerial hyphae and Color thereof: Abundant, Pussywillow gray (5 dc) to ashes (5 fe)
    Soluble pigments: Slightly produced (brown)
2) Glucose-asparagine agar medium
    Growth: Abundant
    Color of substrate hyphae: Dusty yellow (1½ gc) to Rast tan (5 le)
    Formation of aerial hyphae and Color thereof: Abundant, Natural (3 dc) to ashes (5 fe)
    Soluble pigments: Produced (yellow)
3) Glycerol-asparagine agar medium
    Growth: Abundant
    Color of substrate hyphae: Dusty yellow (1½ gc) to Rast tan (5 le)
    Formation of aerial hyphae and Color thereof: Abundant, Cream (1½ ca) to ashes (5 fe)
    Soluble pigments: Produced (yellowish brown)
4) Starch-inorganic salt agar medium
    Growth: Abundant
    Color of substrate hyphae: Powder rose (6 ec) to redwood (6 le)
    Formation of aerial hyphae and Color thereof: Abundant, light gray (c) to ashes (5 fe)
    Soluble pigments: Produced (brown)
5) Tyrosine agar medium
    Growth: Abundant
    Color of substrate hyphae: Olive (1½ ni) to coral rose (6½ ic)
    Formation of aerial hyphae and Color thereof: Abundant, White (a) to gray (e)
    Soluble pigments: None
6) Nutrient agar medium
    Growth: Moderate
    Color of substrate hyphae: Light brown (4 ng) to oak brown (4 pi)
    Formation of aerial hyphae and Color thereof: Little formed
    Soluble pigments: None
7) Yeast-malt agar medium
    Growth: Abundant
    Color of substrate hyphae: Tile red (5 ne) to brick red (5 ng)

Formation of aerial hyphae and Color thereof:
   Abundant, White (a) to Silver gray (3 fe)
Soluble pigments: Produced (brown)

8) Oatmeal agar medium
Growth: Moderate
Color of substrate hyphae: Rast tan (5 le) to brick red (5 ng)
Formation of aerial hyphae and Color thereof:
   Abundant, Gray (g)
Soluble pigments: Produced (brown)

3. Physiological properties:

The temperature range for growth indicates the results of the strain after a 14-day cultivation period. Other items indicate the results after a 2 to 3 week-cultivation at 28° C.

1) Temperature range for growth: 5.5° to 46.5° C.
2) Liquefaction of gelatin: Not observed
3) Hydrolysis of starch: Not observed
4) Coagulation of skim milk powder and peptonization thereof: Not observed
5) Formation of melanoid pigment:
   (i) Peptone-yeast extact-iron agar: Not observed
   (ii) Tyrosine agar: Not observed
6) Utilization of carbon source (basic medium: Pridham Gottlieb-agar medium):

+ indicates that the strain utilizes the carbon source; and
− indicates that the strain did not utilize the carbon source.

| | |
|---|---|
| L-Arabinose: | + |
| D-Xylose: | + |
| D-Glucose: | + |
| Sucrose: | − |
| Raffinose: | − |
| D-Fructose: | + |
| L-Rhamnose: | + |
| Inositol: | + |
| D-Mannitol: | + |

4. Chemotaxonomic properties:
   Optical isomer of diaminopimelic acid in the strain: LL-form Accordingly, the strain is classified into the genus Streptomyces of actinomycetes.

This strain was named Streptomyces sp. E-1625, and it was deposited at the National Institute of Bioscience and Human Technology of the Agency of Industrial Science and Technology under FERM BP-4965 as of Jan. 10, 1995 in terms of the Budapest Treaty.

The microorganism that produces Compound (I) of the present invention is cultivated by a method ordinarily used to cultivate actinomycetes. The medium for cultivating the microorganisms may be any of natural media and synthetic media, so long as it properly contains carbon sources, nitrogen sources, inorganic substances and the like that may be assimilated by the microorganisms.

Examples of the carbon sources include carbohydrates such as glucose, fructose, sucrose, stabilose, starch, dextrin, mannose, maltose and molasses; organic acids such as citric acid, maleic acid, acetic acid and fumaric acid; alcohols such as methanol and ethanol; hydrocarbons such as methane, ethane, propane and n-paraffins; amino acids such as glutamic acid; and glycerol.

Examples of the nitrogen sources include ammonium salts such as ammonium chloride, ammonium sulfate, ammonium nitrate and ammonium phosphate, amino acids such as aspartic acid, glutamine, cystine and alanine, urea, peptone, meat extract, yeast extract, dry yeast, corn steep liquor, soybean powder, cottonseed cakes, soybean casein, cazamino acid and Pharmamedia.

Examples of the inorganic substances include potassium monohydrogenphosphate, potassium dihydrogenphosphate, sodium dihydrogenphosphate, magnesium phosphate, magnesium sulfate, ferrous sulfate, manganese sulfate, copper sulfate, cobalt sulfate, zinc sulfate, nickel sulfate, calcium pantothenate, ammonium molybdate, potassium aluminum sulfate, barium carbonate, calcium carbonate, cobalt chloride and NaCl.

A substance that accelerates proliferation of strains or formation of Compound (I), such asvitamins, for example, thiamine, may be added to the medium as required. Further, a specific substance which is required for the microorganism is added to the medium.

The cultivation is carried out by shaking culture or aerial stirring culture at a temperature of from 20° to 40° C. while maintaining a nearly neutral pH range. Ordinarily, upon cultivation for from 3 to 7 days, Compound (I) is accumulated, reaching at the highest level, and the cultivation is completed.

Compound (I) accumulated in the culture is recovered from the culture by an ordinary method for recovering an Interleukin-1 production inhibiting compound from a culture.

That is, Compound (I) is isolated by extraction of a strain ingredient with a solvent such as acetone or methanol, removal of the strain by filtration or centrifugation, absorption or desorption treatment of an active substance through column chromatography or thin-layer chromatography using an adsorption resin, silica gel, cylanized silica gel, reverse-phase silica gel, aluminum, cellulose, diatomaceous earth, magnesium silicate, gel filter medium or ion-exchange resin, or partition with a suitable solvent.

During the above-mentioned purification step, Compound (I) is detected through silica-gel thin-layer chromatography and then through iodine color development or irradiation with an ultraviolet light of 253.6 nm.

The biological activities of Compound (I) will be described in the following Test Examples.

Test Example 1

Inhibiting Activity of the production of IL-1

With respect to Compound (I) of the present invention, the inhibiting activity of production of IL-1 β derived from THP-1 cells (ATCC No. TIB 202) of a human monocyte was examined. The amount of IL-1 β was determined by the ELISA method.

The THP-1 cells were suspended in an RPMI 1640 culture solution comprising 10% inactivated fetal bovine serum at a concentration of $1 \times 10^5$ cells/ml. The suspension was charged in a 24-well plate at a volume of 1 ml/well. PMA (phorbol 12-myristate 13-acetate, made by Wako Pure Chemical Industries, Ltd.; final concentration 30 nM) was added thereto, and the mixture was cultured in a mixed gas of 5% $CO_2$ and 95% air at 37° C. for 65 hours. The cells were differentiated in a macrophage form.

The cultivation plate was gently washed with a serum-free RPMI 1640 culture solution to remove the cells not adhered thereto, and the residue was cultured for 4 hours in a serum-free RPMI 1640 culture solution (1 ml/well) to which LPS (lipopolysaccharide, made by Difco Laboratories; a final concentration 25 µg/ml) and a compound to be tested were added simultaneously.

After the completion of the cultivation, the amount of IL-1 β which was released in the cultivated supernatant was determined using an IL-1 β determination kit (made by Amersham Corp.).

Percent inhibition of IL-1 production was calculated using the following equation to obtain $IC_{50}$ (50% inhibitory concentration).

Percent inhibition of IL-1 production (%) = $[(A-B)/(A-C)] \times 100$ wherein:
A: amount of IL-1 produced when only LPS is added
B: amount of IL-1 produced when LPS and the compound to be tested are added
C: amount of IL-1 when LPS is not added
The results are shown in Table 1.

TABLE 1

| Compound to be tested | $IC_{50}$ (M) |
|---|---|
| EI-1511-3 | 5.4 |
| EI-1511-5 | 3.6 |
| EI-1625-2 | 5.4 |

As apparent from the results in Table 1, Compound (I) of the present invention have inhibiting activity of the production of IL-1.

Test Example 2
Antibacterial activity

A minimum growth inhibitory concentration (MIC) with respect to various bacteria is shown in Table 2.

TABLE 2

| | MIC (μg/ml) | | |
|---|---|---|---|
| Bacteria to be tested | EI-1511-3 | EI-1511-5 | EI-1625-2 |
| Staphylococcus aureus ATCC 6538P | 20 | 20 | 10 |
| Enterococcus faecium ATCC 10541 | 20 | 20 | 20 |
| Bacillus subtilis No. 10707 | 20 | 20 | 5 |

Antibacterial activity was determined by an agar dilution method using a medium (pH 7.0) comprising 3 g/l bactotrypton (made by Difco Laboratories), 3 g/l meat extract, 1 g/l yeast extract, 1 g/l glucose and 16 g/l agar.

The compound which is used as an IL-1 production inhibitor in the present invention can be administered as such or as a pharmaceutical composition either orally or parenterally. The form of the pharmaceutical composition is a tablet, pill, powder, granule, capsule, suppository, injection or eye drop.

The above-mentioned pharmaceutical composition can be formed by an ordinary method. It may contain various additives such as an excipient, lubricant, binder, disintegrator, suspending agent, isotonic agent, emulsifying agent, absorption accelerator and the like.

The carrier to be used in the pharmaceutical composition can include water, distilled water for injection, physiological saline, glucose, fructose, white sugar, mannitol, lactose, starch, corn starch, potato starch, cellulose, methyl cellulose, carboxymethyl cellulose, hydroxypropyl cellulose, arginic acid, talc, sodium citrate, calcium carbonate, calcium hydrogenphosphate, magnesium stearate, urea, silicone resin, sorbitan aliphatic, acid ester and/or glycerin aliphatic acid ester. These carries can be appropriately selected depending on the preparation from.

The dose of the interleukin-1 production inhibitor which is used for the above-mentioned purpose is determined depending on a desired therapeutic effect, administration method, administration period, and age and weight of patients. It is usually from 0.01 to 2 mg/kg a day for an adult in peroral or parenteral administration (for example, rectal administration by injection, drops or suppository, or application to the skin.)

The present invention will be illustrated specifically by referring to the following Examples and Preparation Examples.

EXAMPLE 1

Streptomyces sp. E-1511 (FERMBP-4729) was used as a seed strain. A medium (pH 7.0) comprising 10 g/l glucose, 10 g/l soluble starch, 3 g/l beef extract (made by Kyokuto Seiyaku Kogyo K.K.), 5 g/l powdery yeast extract S (made by Nippon Seiyaku K.K.), 5 g/l bactotryptone, 1 g/l potassium dihydrogenphosphate, 0.5 g/l magnesium sulfate 7-hydrate and 0.5 g/l magnesium phosphate 8 hydrate was used as a first medium.

One loopful of the strain was inoculated into 10 ml of the first medium filled in a 50-milliliter test tube. The strain was cultivated with shaking in each of two such tubes (total amount of the medium—20 ml) at 28° C. for 3 days.

Five milliliters of the first culture was inoculated into 50 ml of a second medium filled in a 300-milliliter Erlenmeyer flask. The culture was put into each of three such flasks (total amount of the medium—150 ml), and cultivated at 28° C. for 2 days with shaking (second cultivation). The second medium had the same formulation as that of the first medium.

Fifty milliliters of the obtained second culture was inoculated into 500 ml of a third medium filled in a 2-liter Erlenmeyer flask. The culture was cultivated in each of three such flasks (total amount of the medium—1.5 liters) at 28° C. for 2 days with shaking (third cultivation). The third medium had the same formulation as that of the second medium.

The obtained third culture (1.5 liters) was inoculated into 17 liters of a main fermentation medium filled in a 30-liter stainless steel jar fermenter. A medium (pH7.0) comprising 10 (v/v) % of Diaion HP-20 (made by Mitsubishi Chemical Corp.), 40 g/l soluble starch, 10 g/l soybean powder, 5 g/l corn steep liquor, 5 g/l dry yeast, 0.5 g/l potassium dihydrogenphosphate, 0.5 g/l magnesium phosphate 8 hydrate, 10 μg/l zinc sulfate 7 hydrate, 1 μg/l cobalt chloride 6 hydrate and 1 μg/l nickel sulfate was used as a main fermentation medium. The main fermentative cultivation was conducted at 28° C. for 6 days through aerial stirring (number of rotations—300 rpm, amount of gas: 18 L/min).

The obtained main fermentative culture (17 liters) was filtered through a 150 μm-mesh sieve to separate Diaion HP-20. Diaion HP-20 separated was placed on a Diaion HP-20 column (1 liter), washed with 6 liters of water, and eluted with a mixed solvent of methanol and acetone (7:3). The fraction containing EI-1511 was collected, concentrated to dryness under reduced pressure and dissolved in 2 liters of methanol. To 1 liter of the solution were added 10 g of ODS (ODS-AQ-S50, made by YMC, 30 mm (diameter)× 500 mm). The mixture was then concentrated to dryness, put into a column filled with 400 ml of ODS (ODS-AQ-S50, made by YMC, 30 mm (diameter) ×500 mm), washed with a mixed solvent of 30% methanol and 0.1% acetic acid, and eluted with a mixed solvent of 80% methanol and 0.1% acetic acid. The fraction containing EI-1511 was collected, diluted to 1.5 times with water, passed through a column filled with 400 ml of ODS filled in a column (ODS-AQ-S50, made by YMC, 30 mm (diameter)×500 mm), adsorbed thereon, and then eluted with a mixed solvent of 65% acetone and 0.1% acetic acid.

The fraction containing EI-1511 was collected, diluted to 1.5 times with water, then passed through an ODS column (ODS-AQ-S50, made by YMC, 30 mm (diameter)×500 mm), adsorbed thereon, and eluted with a mixed solvent of 65% acetone and 0.1% acetic acid to separate the fraction containing EI-1511-3 and the fraction containing EI-1511-5.

The fraction containing EI-1511-3 was diluted to 1.5 times with water, then passed through an ODS column (ODS-AQ-S50, made by YMC, 30 mm (diameter)×500 mm), adsorbed thereon, and then eluted with a mixed solvent of 60% aceotone and 0.1% acetic acid. The fraction containing EI-1511-3 was collected, then diluted again to 1.5 times with water, passed through an ODS column (ODS-AQ-S50, made by YMC, 30 mm (diameter)×500 mm), adsorbed thereon, and eluted with a mixed solvent of 60% acetone and 0.1% acetic acid to obtain 90 mg of EI-1511-3.

The fraction containing EI-1511-5 was diluted to 1.5 times with water, passed through an ODS column (ODS-T, made by Nomura Kagaku K.K., 30 mm (diameter)×500 mm), adsorbed thereon, and eluted with a mixed solvent of 60% acetone and 0.1% acetic acid to collect the fraction containing EI-1511-5. The fraction containing EI-1511-5 was diluted again to 1.5 times with water, passed through an ODS column (ODS-T, made by Nomura Kagaku K.K., 30 mm (diameter)×500 mm), adsorbed thereon, and eluted with a mixed solvent of 60% acetone and 0.1% acetic acid to obtain 15 mg of EI-1511-5.

During the above-mentioned procedure, the compounds EI-1511-3 and 1511-5 were detected through silica gel thin-layer chromatography and then iodine color development or irradiation with an ultraviolet light of 253.6 nm.

EXAMPLE 2

Streptomyces sp. E-1625 (FERM BP-4965) was used as a strain. A medium (pH 7.0) containing 10 g/l glucose, 10 g/l soluble starch, 3 g/l beef extract (made by Kyokuto Seiyaku Kogyo K.K.), 5 g/l powdery yeast extract S (made by Nippon Seiyaku K.K.), 5 g/l bactotryptone, 1 g/l potassium dihydrogenphosphate, 0.5 g/l magnesium sulfate 7 hydrate and 0.5 g/l magnesium phosphate 8 hydrate was used as a first medium.

One loopful of the strain was inoculated into 10 ml of the first medium filled in a 50-milliliter test tube. The strain was cultivated with shaking in each of two such test tubes (total amount of the medium—20 ml) at 28° C. for 2 days.

Five milliliters of the first culture were inoculated into 50 ml of a second medium filled in a 300-milliliter Erlenmeyer flask. The culture was put into each of four such flasks (total amount of the medium—200 ml), and cultivated at 28° C. for 2 days with shaking (second cultivation). The second medium had the same formulation as that of the first medium.

Five milliliters of the obtained second culture was inoculated into 50 ml of a main fermentation medium filled in a 300-milliliter Erlenmeyer flask. The culture was put into each of forty such flasks (total amount of the medium—2 liters) with shaking at 28° C. for 6 days (main fermentative cultivation). A medium (pH 7.0) containing 10 (v/v) % of Diaion HP-20 (made by Mitsubishi Chemical Corp.), 40 g/l soluble starch, 10 g/l soybean powder, 5 g/l corn steep liquor, 5 g/l dry yeast, 5 g/l potassium dihydrogenphosphate, 0.5 g/l magnesium phosphate 8 hydrate, 10 µg/l zinc sulfate 7 hydrate, 1 µg/l cobalt chloride 6 hydrate and 1 µg/l nickel sulfate was used as a main fermentation medium.

Two liters of the obtained main fermentation culture was centrifuged to separate the cells. To the cells was added 2 liters of methanol, and the mixture was stirred and then filtered. The filtrate was diluted to 5 times with water, then passed through a Diaion HP-20 column (400 ml), absorbed thereon, washed with 1.6 liters of 20% methanol, and eluted with a mixed solvent of methanol and acetone (7:3).

The fraction containing EI-1625-2 was collected, and concentrated under reduced pressure to remove acetone. Water was added to the residue to form a 20% methanol solution. The solution was passed in two divided portions through a Diaion HP-20SS column (made by Mitsubishi Chemical Corp.), adsorbed thereon, and then eluted with a mixed solvent of 0.1% acetic acid and methanol at a linear concentration gradient of from 20 to 100%.

The fractions containing EI-1625-2 were combined and diluted to 2 times with water. The thus-obtained solution was passed in two divided portions through an ODS column (ODS-AQ-S50, made by YMC, 30 mm (diameter)×500 mm), adsorbed thereon, and then eluted with a solution of 75% methanol and 0.1% acetic acid.

The fractions containing EI-1625-2 were collected, concentrated to dryness under reduced pressure, dissolved in 5 ml of 75% methanol, passes through an ODS column (ODS-AQ-S50, made by YMC, 30 mm (diameter)×500 mm), adsorbed thereon, and eluted with a solution of 75% methanol and 0.1% acetic acid to obtain 20 mg of EI-1625-2.

During the above-mentioned procedure, EI-1625-2 was detected through silica gel thin-layer chromatography and then through iodine color development or irradiation with an ultraviolet light of 253.6 nm.

Preparation Example 1: Tablet

| | |
|---|---|
| EI-1511-3 | 100 g |
| Lactose | 40 g |
| Corn starch | 18 g |
| Carboxymethyl cellulose calcium | 10 g |

The mixture having the above-mentioned formulation was kneaded with 42 ml of a 10% hydroxypropyl cellulose solution. The thus-obtained mixture was pulverized by means of a pushing pulverizer fitted with a 1-millimeter basket. The resulting powder was formed into granules with the addition of magnesium stearate, and a tablet (170 mg) containing 100 mg of EI-1511-3 and having a diameter of 8 mm was prepared in a usual manner.

Preparation Example 2: Tablet

| | |
|---|---|
| EI-1511-5 | 100 g |
| Lactose | 40 g |
| Corn starch | 18 g |
| Carboxymethyl cellulose calcium | 10 g |

Using the mixture having the above-mentioned formulation, a tablet (170 mg) containing 100 mg of EI-1511-5 and having a diameter of 8 mm was prepared in the same manner as in Preparation Example 1.

Preparation Example 3.: Tablet

| | |
|---|---|
| EI-1625-2 | 100 g |
| Lactose | 40 g |
| Corn starch | 18 g |
| Carboxymethyl cellulose calcium | 10 g |

Using the mixture having the above-mentioned formulation, a tablet (170 mg) containing 100 mg of EI-1625-2 and having a diameter of 8 mm was prepared in the same manner as in Preparation Example 1.

Preparation Example 4: Capsule

|  |  |
|---|---|
| EI-1511-3 | 50 g |
| Lactose | 80 g |
| Potato starch | 38 g |

The mixture having the above-mentioned formulation was kneaded with 42 ml of a 10% hydroxypropyl cellulose solution. The thus-obtained mixture was pulverized in the same manner as in Preparation Example 1, and magnesium stearate was added to the powder. A capsule (170 mg) containing 50 mg of EI-1511-3 was prepared in a usual manner.

Preparation Example 5: Capsule

|  |  |
|---|---|
| EI-1511-5 | 50 g |
| Lactose | 80 g |
| Potato starch | 38 g |

Using the mixture having he above-mentioned formulation, a capsule (170 mg) containing 50 mg of EI-1511-5 was prepared in the same manner as in Preparation Example 4.

Preparation Example 6: Capsule

|  |  |
|---|---|
| EI-1625-2 | 50 g |
| Lactose | 80 g |
| Potato starch | 38 g |

Using the mixture having the above-mentioned formulation, a capsule (170 mg) containing 50 mg of EI-1625-2 was prepared in the same manner as in preparation Example 4.

Preparation Example 7: Soft capsule

Ten grams of EI-1511-3 was dissolved in 100 g of soybean oil, and the obtained solution was poured into a capsule in a usual manner to prepare a soft capsule containing 10 mg of EI-1511-3.

Preparation Example 8: Soft capsule

Ten grams of EI-1511-5 was dissolved in 100 g of soybean oil, and the obtained solution was poured into a capsule in a usual manner to prepare a soft capsule containing 10 mg of EI-1511-5.

Preparation Example 9: Soft capsule

Ten grams of EI-1625-2 was dissolved in 100 g of soybean oil, and the obtained solution was poured into a capsule in a usual manner to prepare a soft capsule containing 10 mg of EI-1625-2.

What is claimed:

1. A compound represented by formula (I)

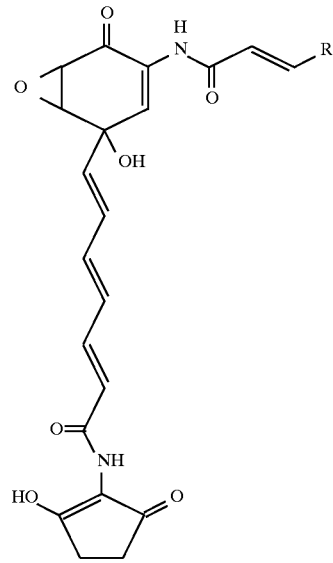

(I)

wherein R denotes 4-methyl-1-pentenyl, 5-methyl-1,3-heptadienyl or 1-methylpentanyl.

2. A pharmaceutical composition comprising, as an active ingredient, the compound claimed in claim 1, and a pharmaceutically acceptable carrier.

3. A pharmaceutical composition according to claim 2, wherein said composition is in a form selected from the group consisting of a tablet, pill, powder, granule, capsule, suppository, injection solution and eye drop.

4. A pharmaceutical composition according to claim 2, wherein said pharmaceutically acceptable carrier comprises a substance selected from the group consisting of water, distilled water, saline, glucose, fructose, white sugar, mannitol, lactose, starch, cellulose, alginic acid, talc, sodium citrate, calcium carbonate, calcium hydrogenphosphate, magnesium stearate, urea, silicone resin, sorbitan aliphatic acid ester and glycerin aliphatic acid ester.

5. A pharmaceutical composition according to claim 2, wherein said composition is in the form of a tablet comprising the compound of formula I and lactose.

6. A pharmaceutical composition according to claim 2, wherein said composition is in the form of a capsule comprising the compound of formula I and lactose.

7. A pharmaceutical composition according to claim 2, wherein said composition is in the form of a soft capsule comprising the compound of formula I and soy bean oil.

8. A compound according to claim 1, wherein said compound inhibits the production of interleukin 1-beta converting enzyme.

* * * * *